US00PP10099P

United States Patent [19]

Kerridge

[11] Patent Number: Plant 10,099

[45] Date of Patent: Nov. 4, 1997

[54] PLANT VARIETY OF PRIMULA NAMED 'YVONNE'

[76] Inventor: John Kerridge, #1102 4660 W. 10th Avenue, Vancouver, B.C., Canada, V6R 2J6

[21] Appl. No.: 661,098

[22] Filed: Jun. 10, 1996

[51] Int. Cl.[6] ..... A01H 5/00

[52] U.S. Cl. ..... Plt./68.1

[58] Field of Search ..... Plt./68.1

*Primary Examiner*—James R. Feyrer
*Assistant Examiner*—Kent L. Bell
*Attorney, Agent, or Firm*—Christie, Parker & Hale, LLP

[57] ABSTRACT

A new plant variety of Primula producing flowers larger than common gold-laced polyanthus Primula, more suitable for garden usage.

2 Drawing Sheets

BACKGROUND OF THE INVENTION

The present invention relates to a new and distinct variety of Primula which was created by crossing as seed parent the common gold-laced polyanthus Primula with an unknown garden variety Primula having large, deep red flowers. The first generation progeny was crossed back to the gold-laced polyanthus Primula to produce the new variety. The varietal domination of the new variety is 'Yvonne'.

Polyanthus Primula is a perennial plant that blooms in the Spring and has a crown of leaves, each on a petiole extending from a short rhizome or root stock, typically without rachis. The foliage of 'Yvonne' resembles polyanthus Primula.

SUMMARY OF THE INVENTION

The general morphology of the new variety is similar to polyanthus Primula, but differs in significant respects. Among the novel characteristics of 'Yvonne' which distinguish it from the gold-laced polyanthus Primula and other varieties of Primula of which I am aware, are the size of the flowers of the new variety, which are nominally about 2.5 cm as compared to 1 to 1.5 cm for the gold-laced Primula, the general flower coloration and the cold hardiness of the plant, which has survived temperatures of −14° C. without snow cover. The larger flower size of the new variety makes it more desireable for usage as garden plants than gold-laced Primula with its much smaller size flowers.

Asexual reproduction by tissue culture micropropagation in Mount Vernon, Wash., shows that the foregoing and other distinguishing characteristics come true to form and are established and transmitted through succeeding propagations.

BRIEF DESCRIPTION OF ILLUSTRATIONS

The accompanying illustrations show typical specimens of the flowers of the new variety in different stages of development, and a comparison of the size of flowers of common gold-laced polyanthus Primula and the new variety, depicted in color as nearly true as it is reasonably possible to make the same in color illustrations of this character. The larger flowers in the illustration are of the new variety, on the right in the illustration; the smaller flowers of common gold-laced polyanthus Primula are on the left.

DETAILED DESCRIPTION OF THE NEW VARIETY

The following is a detailed description of the new variety with color terminology in accordance with The Royal Horticultural Society Colour Chart (R.H.S.C.C.), unless otherwise indicated. The terminology used for color descriptions herein refers to plate numbers in the aforementioned colour chart.

The following observations were made of specimens grown under glass in Mount Vernon, Wash., during the month of March. Phenotypic expression may vary with light, environmental and cultural conditions.

PLANT

A. Form: Upright.

B. Growth: Vigorous, typical of polyanthus Primula, forming crowns suitable for division.
   *Height.*—About 22 to 26 cm.

C. Foliage:
   *Size.*—About 12 to 16 cm.
   *Quantity.*—Typical for polyanthus Primula.
   *Color.*—New foliage: Upper side: Medium green, near 139C. to near 139D. Underside: Light green, lighter than upper side. Old Foliage: Upper side: Medium green, near 139B to near 139D. Underside: Light green, lighter than upper side.
   *Shape.*—Elliptic.
   *Texture.*—Upper side: Wrinkled and veined. Underside: Wrinkled and veined.
   *Edge.*—Finely notched, crenated.
   *Resistance to disease.*—Typical of polyanthus Primula; i.e. subject to mollusc attack, cutworms; no special disease susceptibility observed.

D. Winter hardiness: Has shown hardiness in open ground without snow cover to minus 14° C. in Pacific Northwest.

FLOWER

A. Inflorescence: Terminal, umbellate; cluster of flowers in a spreading, symmetrical umbel; about 5 to 9 lobed flowers ("pips") with all pedicels arising from a common point on a sturdy peduncle.

B. Bud: Elongated, trumpet shaped flower "stalk" (elongated pedicel) terminating in visible undersurface of petals seen as an upper end a near-black region which changes to mahogany red as the flower opens.

C. Bloom: As the flower opens and ages, the petal top surface shows a near-black on the region of the petal top surface which lightens and becomes near 185A at the center with near 16A at the edges and margins; the margins combine with a central medial line, also near 16A, between petal segments; there is a golden central eye, near 16A, occupying about ½ of the radius of each bloom. The petal undersurface corresponds in color to the petal top surface but the central yellow region may be obscured by sepals. It is common to have flowers with dark, near-black petals similar to coloration of polyanthus Primula and flowers with petals as described above on plants at the same time. Generally, the near-black or very dark purple black coloring, lightens to red as the flowers age. The flowers are referred to as "thrum-eyed" because the regularly arranged stamens occupy the mouth of the tube.

REPRODUCTIVE ORGANS

A. Stamens, filaments and anthers:

*Arrangement.*—Arranged around the mouth of the tube, with the styles hidden (thrum-eyed).

*Color.*—Stamens are golden yellow, near 16A.

B. Pollen: Golden yellow, near 16A; lightens with age.

C. Styles: Not visible, typical of polyanthus Primula.

D. Stigmas: Not visible.

I claim:

1. A new and distinct plant variety of Primula, substantially as shown and described.

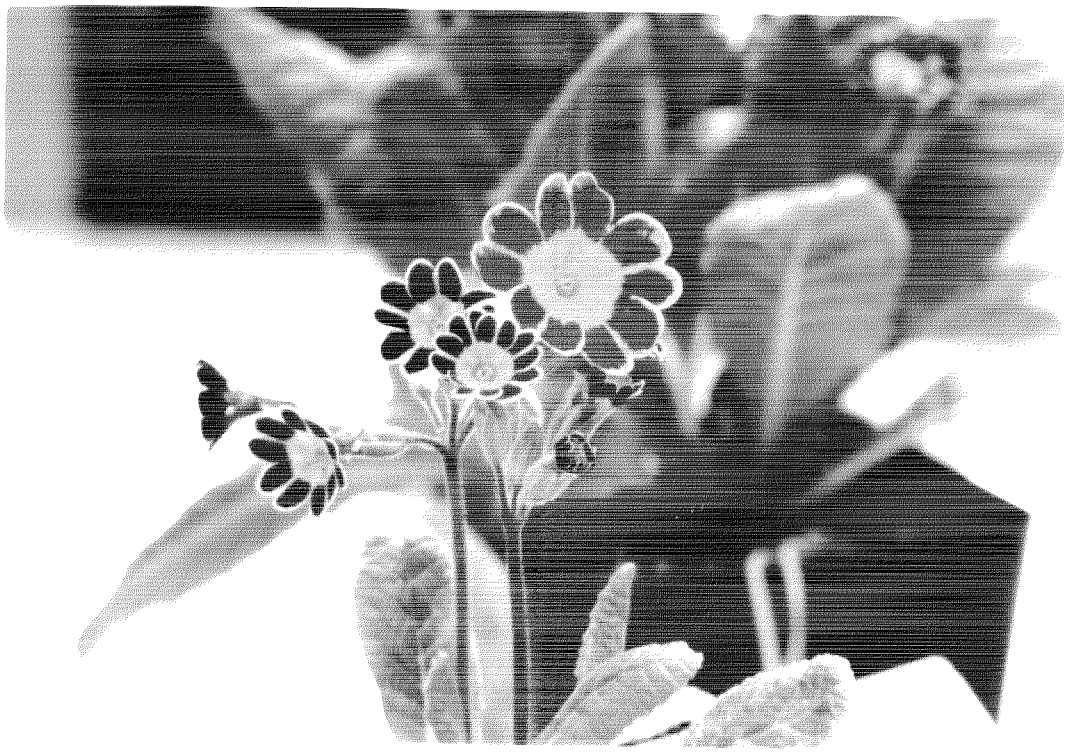

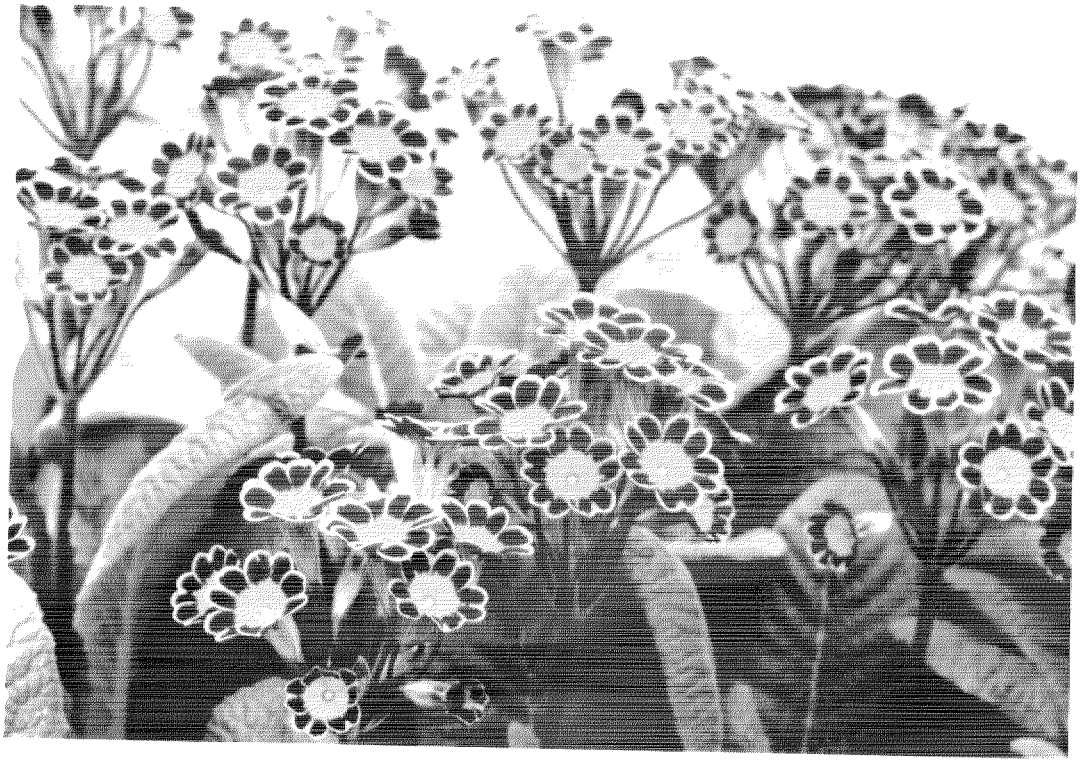

* * * * *